United States Patent [19]
Karrer

[11] 3,950,328
[45] Apr. 13, 1976

[54] TERPENE ARYL ETHERS

[75] Inventor: Friedrich Karrer, Basel, Switzerland

[73] Assignee: Ciba-Geigy Corporation, Ardsley, N.Y.

[22] Filed: May 16, 1973

[21] Appl. No.: 360,854

Related U.S. Application Data

[63] Continuation-in-part of Ser. No. 190,307, Oct. 18, 1971, abandoned.

[30] Foreign Application Priority Data

Oct. 20, 1970 Switzerland.................... 15436/70
Aug. 23, 1971 Switzerland.................... 12321/71

[52] U.S. Cl. ............ 260/240 H; 424/278; 424/301; 424/320; 424/340; 260/455 R; 260/613 R
[51] Int. Cl.² ..................................... C07D 303/18
[58] Field of Search .............................. 260/240 H

[56] References Cited
UNITED STATES PATENTS

| | | |
|---|---|---|
| 3,718,686 | 2/1973 | Chodnekar et al. ........ 260/240 H X |
| 3,769,320 | 10/1973 | Chodnekar et al. ............ 260/473 R |
| 3,773,797 | 11/1973 | Chodnekar et al. ............ 260/348 R |
| 3,880,935 | 4/1975 | Chodnekar et al. ............ 260/613 D |

*Primary Examiner*—John D. Randolph
*Attorney, Agent, or Firm*—Harry Falber; Frederick H. Rabin

[57] ABSTRACT

New terpene aryl ethers of the formula

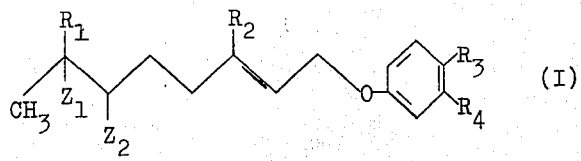

wherein
$Z_1$ and $Z_2$ together form a carbon-carbon-bond or together are an oxygen bridge,
$R_1$ and $R_2$ are each methyl or ethyl and
$R_3$ represents allyloxy, β-chlorallyloxy, γ-chlorallyloxy, Methallyloxy, acetylamino, benzoyl, benzyl, phenoxy or (methylthio)-carbonyl and
$R_4$ is hydrogen or
$R_3$ is hydrogen and $R_4$ represents propargyloxy and their use for combating insects are disclosed.

2 Claims, No Drawings

NEW TERPENE ARYL ETHERS

CROSS REFERENCE TO RELATED APPLICATIONS

This Application is a continuation-in-part of Patent application Ser. No. 190,307, filed Oct. 18, 1971, now abandoned.

The present invention relates to new terpene aryl ethers and their use for combating insects.

The new terpene aryl ethers have the formula

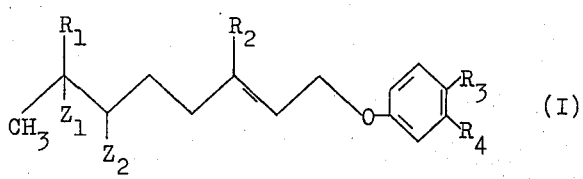

wherein
- $Z_1$ and $Z_2$ together form a carbon-carbon-bond or together are an oxygen bridge,
- $R_1$ and $R_2$ are each methyl or ethyl and
- $R_3$ represents allyloxy, β-chlorallyloxy, γ-chlorallyloxy, Methallyloxy, acetylamino, benzoyl, benzyl, phenoxy or (methylthio)-carbonyl and
- $R_4$ is hydrogen or
- $R_3$ is hydrogen and $R_4$ represents propargyloxy.

For the manufacture of compounds of the formula I takes place in fashion known per se by the following reactions, preferably with equimolecular quantities of the starting material; if desired, however, an excess of one or more of the reactants can be used:

solvent such as 1,2-dimethoxyethane, tetrahydrofurane, dioxane, dimethylformamide, dimethylsulfoxide, sulfolane or a dialkylether, preferably, however in 1,2-dimethoxyethane, by slow addition of an equivalent of an acid acceptor such as an alkali or alkaline earth hydroxide or alkali or alkaline earth carbonate, or alkali alkoxide or alkali hydride with stirring at room temperature and optionally with subsequent warming. The isolation of the terpene aryl ether then takes place by known techniques. Amongst alkalis there should be understood here particularly potassium and sodium and among alkaline earth metals calcium.

Reaction 2), i.e. the transfer of the terpenoid arylether into their 6,7 epoxy derivatives are preferably carried out with cooling in an inert solvent medium such as for example a chlorinated hydrocarbon, with an epoxidising agent, for example a peracid. With the use of one mole of peracid, then as a result of the steric factor predominantly the 6,7 epoxy derivative is formed. The 6,7 epoxy derivatives can also be obtained with N-bromosuccinimide in a mixture of water with a solvent such as tetrahydrofurane, 1,2-dimethoxyethane, dioxane, or tert. butanol in homogeneous or hetragenerous phase with subsequent treatment of the intermediary bromohydrin which arises with an alkaline agent such as an alkali carbonate, alkali hydroxide or an alkali alkoxide. Among alkalis particularly sodium and potassium are to be understood.

By the term peracid, there is to be understood predominantly low peralkane acids with 1–6 carbon atoms, e.g. peracetic acid, as well as aromatic peracids such as perbenzoic acid, monoperphthalic acid, and particularly m-chloroperbenzoic aicd, As basic reagents for transforming a bromohydrin into 6,7 epoxy

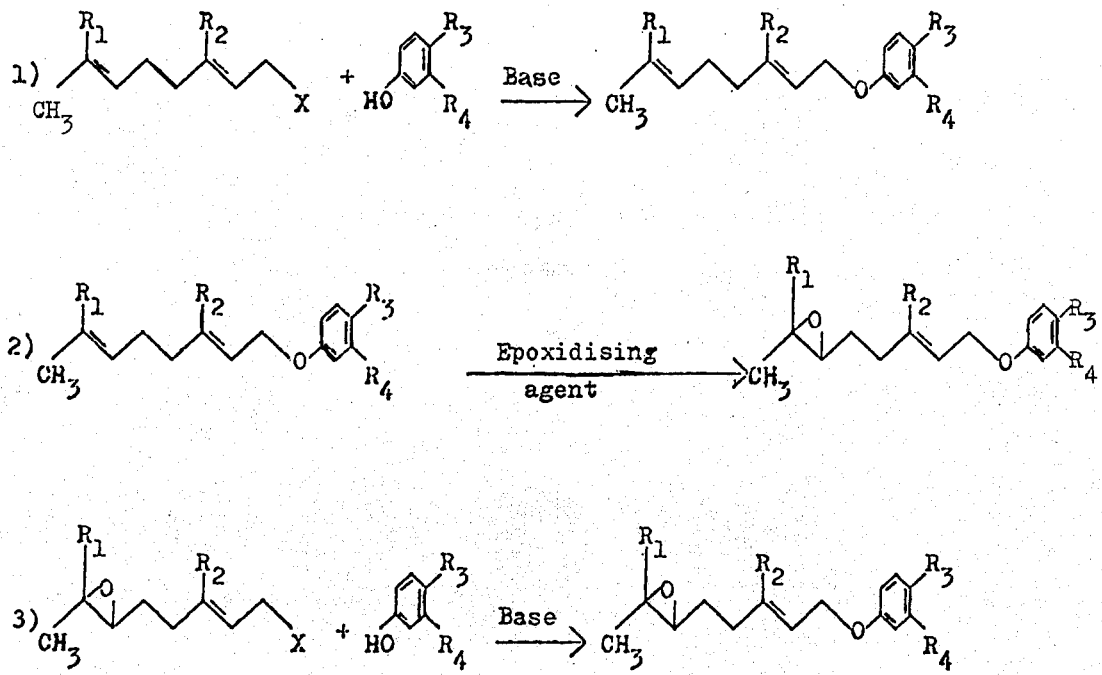

In these equations X is halogen, preferably chlorine or bromine. Reactions 1) and 3), i.e. the reactions with mixtures of geometrical isomers of the reactive allylic halides with the desired phenol are carried out in a derivatives alkali carbonates, alkali hydroxydes, and alkali alkoxides can be used.

As further variation in the synthesis there should be mentioned the reaction of a 1-(4-hydroxy) or 1(3- hydroxy) phenoxy-3,7-dialkyl-2,6-octa or nona-diene with a halo derivatives (in the presence of a base, e.g. a tertiary amine, alkali carbonate or alkali hydroxyde), to a phenol diether, of the general formulae II to V:

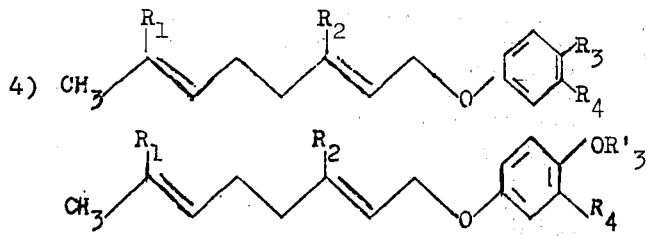

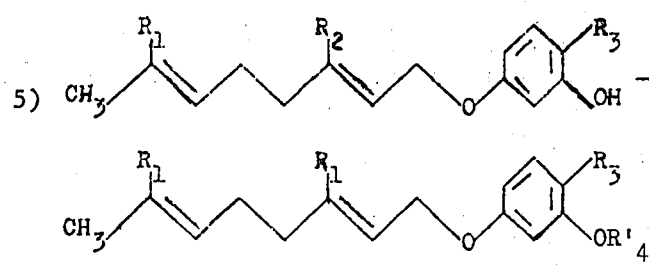

Analogously the 1-(4-hydroxy) or 1-(3-hydroxy) phenoxy-3,7-dialkyl-6-octene or 6-nonene compounds can be transformed to phenol diethers.

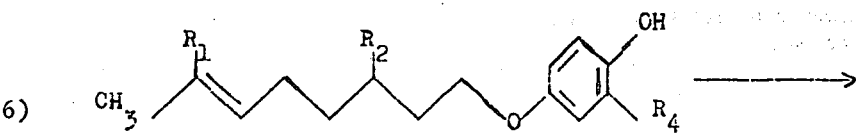

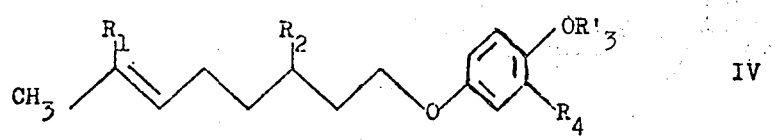

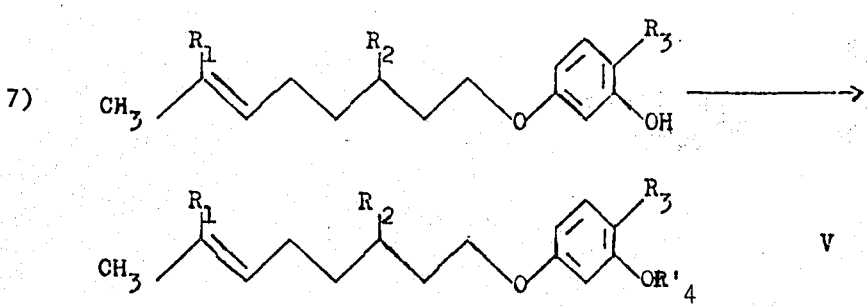

The so obtained phenyl diethers, can then be transformed with an epoxidising agent in the cold in an inert solvent medium into the 6, 7 epoxy derivative.

In formulae II to V $R'_3$ is allyl, β-chloroallyl, γ-chlorallyl, methallyl and $R'_4$ Propargyl.

The substients $R_1$ to $R_4$ (in reactions 1 to 7) have the meaning given for formula I.

In the manufacture of compound of formula I as a result of the alkyl halides used for the synthesis all possible geometrical isomers form. The compounds described are in the form of mixtures of the geometrical isomers which are obtained by the synthesis.

The active substances of formula I are suitable for combating most varied insects. In contrast to most previously known insecticides, which rapidly kill, paralyse or drive away the animals working as contact or ingestion poisons, the active substances of formula I influence the development.

The new terpenoid arylethers can be used above all for combating the following plant, stored product and hygiene insects of the order and families:

| | |
|---|---|
| Orthoptera | Acrididae |
| | Gryllidae |
| | Blattidae |
| Isoptera | Kalotermitidae |
| Hemiptera | Miridae |
| | Piesmidae |
| | Lygaeidae |
| | Phyrrhocoridae |
| | Pentatomidae |
| | Cimicidae |
| | Reduviidae |
| | Jassidae |
| | Eriosomatidae |
| | Lecaniidae |
| Coleoptera | Carabidae |
| | Elateridae |
| | Coccinellidae |
| | Tenebrionidae |
| | Dermestidae |
| | Cucujiidae |
| | Chrysomelidae |
| | Curculionidae |
| | Scolytidae |
| | Scarabaeidae |
| Lepidoptera | Pyralidae |
| | Phyticidae |
| | Pyraustidae |
| | Crambidae |
| | Tortricidae |
| | Galleriidae |
| | Lyonetiidae |
| | Yponomeutidae |
| | Pieridae |
| | Plutallidae |
| | Lymantriidae |
| | Noctuidae |
| Diptera | Culicidae |
| | Simuliidae |
| | Tipulidae |

The compounds of formula I can be used alone or together with suitable carriers and or additive materials. Suitable carriers and additive materials can be solid or liquid and correspond to the customary materials used in formulation technique, e.g. natural or regenerated materials, solvents, dispersing agents, wetting agents, adhesives, thickeners, binders and/or fertilisers.

The manufacture of agents according to the invention takes place in known fashion by intimate mixing and/or milling of active substances of formula I with suitable carriers, optionally with the addition of dispersing agents or solvents inert to the active substance. The active substances can be present and be used in the following use forms:

| | |
|---|---|
| Solid use forms: | dusting agents, spreading agents, granulates, coated granules, impregnated granules and homogeneous granules. |
| Liquid use forms: | |
| a) Active substance concentrates dispersible in water: | wettable powders, pastes, emulsions; |
| b) solutions. | |

For the manufacture of solid use forms (dusting agents, spreading agents) the active substances are mixed with solid carriers. As carriers there are, for example, kaolin, talcum, bolus, loess, chalk, limestone, limestone gravel, ataclay, dolomite, diatomaceous earth, precipitated silica, alkaline earth metal silicates, sodium and potassium aluminium silicates (feldspars and mica), calcium and magnesium sulphates, magnesium oxide, ground plastics materials, fertilisers such as ammonium sulphate, ammonium phosphate, ammonium nitrate, urea, ground vegetable products such as crop flour, bark flour, wood flour, nutshell flour, cellulose powder, residues from plant extraction, active carbon etc., each being usable per se or in admixture with others.

Granulates can be made very easily by dissolving an active substance according to Formula I in an organic solvent medium, applying the solution so obtained to a granulated material such as attapulgite, $SiO_2$, lime, bentonite etc. and then evaporating the organic solvent medium again.

Polymeric granulates can also be made by mixing the active substance of Formula I with polymerisable compounds (urea/formaldehyde, dicyandiamide/formaldehyde, melamine/formaldehyde or others) and then carrying out a careful polymerisation which does not affect the active substance, and wherein during the gel-forming stage, granulation is carried out. It is more favourable to impregnate preformed porous polymer granules (urea/formaldehyde, polyacrylonitrile, polyester and others) with a given surface area and favourably predetermined adsorption/desorption ratio with the active substance, e.g. in the form of a solution (in a low-boiling solvent) and then to remove the solvent. Such polymer granulates can be used in the form of microgranulates of bulk density of preferably 300 to 600 g/liter with the aid of dusting apparatus. Dusting can be carried out over extended surfaces of useful plant cultures with the aid of aircraft.

Granulates can also be obtained by compacting the carrier material with the active material and additive materials and then breaking up the compact.

These mixtures can furthermore contain additives stabilising the active substance and/or non-ionic, anion active or cation active materials, which, for example, improve the adherence of the active substance to plants and plant parts (adhesives and glues) and or guarantee better penetration (wetting agents) or dispersability (dispersing agents).

The following substances may, for example, be used: Olein-lime mixtures, cellulose derivatives (methyl cellulose, carboxymethyl cellulose), hydroxyethyleneglycol ethers of mono- and dialkyl phenols with 5–15 ethylene oxide groups per molecule and 8–9 carbon atoms in the alkyl group, lignin sulphonic acids, their alkali and alkaline earth salts, polyethylene glycol ethers (Carbowaxes), fatty alcohol polyglycol ethers with 5–20 ethylene oxide groups per molecule and 8–18 carbon atoms in the fatty alcohol part, condensation products of ethylene oxide, propylene oxide, polyvinyl pyrrolidone, polyvinyl alcohols, condensation products of urea - formaldehyde as well as latex products.

Active substance concentrates dispersible in water, i.e. wettable powders, pastes and emulsion concentrates are materials which can be diluted with water to any desired concentration. They consist of active agent, carrier, optionally additives stabilising the active substance, surface active agents and anti-foaming agents, and optionally solvents.

The wettable powders and pastes are obtained by mixing and/or milling to homogeneity the active substance with dispersing agents and powder form carriers in suitable apparatus. As carriers, for example the materials mentioned above for solid use forms can be used. In some cases it is advantageous to use mixtures of various carriers. As dispersing agents there can be used, for example: condensation products of sulphonated naphthalene and sulphonated naphthalene derivatives with formaldehyde, condensation products of naphthalene or of naphthalene sulphonic acids with phenol and formaldehyde, as well as alkali, ammonium and alkaline earth metal salts of di-t-butyl-naphthalene sulphonic acids, fatty alcohol sulphates, such as salts of sulphonated hexadecanols, heptadecanols, octadecanols and salts of sulphated fatty alcohol glycol ethers, the sodium salt of oleyl methyl tauride, di-tertiary acetylene glycols, dialkyldilauryl ammonium chloride and fatty acid alkali and alkaline earth salts.

As anti-foaming agents, silicones may be used.

The active substances are so mixed with the above noted additives, milled, sieved and graded that for wettable powders the solid part has a particle size of 0.02 to 0.04 mm, and in the pastes does not exceed 0.03 mm. For the manufacture of emulsion concentrates and pastes dispersing agents as set forth in the preceding paragraphs are used, organic solvents and water. As solvents, there are, for example, alcohols, benzene, xylenes, toluene, dimethyl sulphoxide and mineral oil fractions boiling in the range 120° to 350°C. The solvent medium must be practically odourless, non-phytotoxic and inert with respect to the active substances.

Furthermore, the agents according to the invention can be used in the form of solutions. For this, one or more active substances of Formula I is dissolved in suitable organic solvents, solvent mixes or water. As organic solvent there can be used aliphatic and aromatic hydrocarbons, their chlorinated derivatives, alkyl naphthalenes, mineral oils, alone or in admixture with one another.

The content of active substance in the agents noted above lies between 0.02 and 95 percent, but it is to be noted that in application from aircraft or by means of other suitable application devices, concentrations of up to 99.5 percent or even pure active substance could be used.

The active substances of Formula I can, for example, be formulated as follows:

Dusting agent: for the manufacture of an a) 5 percent and b) 2 percent dusting agent, the following materials were used.

a)
5 parts active substance
95 parts talcum b)
2 parts active substance
1 part highly disperse silica
97 parts talcum.

The active substances were mixed with the carrier materials and milled.

Granulate: for manufacturing a 5% granulate, the following materials were used:
5 parts active substance
0.25 parts epichlorohydrin
0.25 parts cetyl polyglycol ether
3.50 parts polyethylene glycol ("Carbowax")
91 parts kaolin (particle size 0.3–0.8 mm).

The active substance was mixed with epichlorohydrin and dissolved in 6 parts acetone, whereafter the polyethylene glycol and cetyl polyglycol ether were added. The solution thus obtained was sprayed onto kaolin and the acetone then evaporated in vacuo.

Wettable powder: for manufacturing an a) 40 percent, and b) and c) 25 percent and d) 10 percent wettable powder, the following components were used:

a)
40 parts active substance
5 parts lignin sulphonic acid, sodium salt
1 part dibutyl naphthalene sulphonic acid, sodium salt
54 parts silica;

b)
25 parts active substance
4.5 parts calcium lignosulphonate
1.9 parts champagne chalk-hydroxyethyl cellulose mixture (1:1)
1.5 parts sodium dibutyl naphthalene sulphonate
19.5 parts silica
19.5 parts champagne chalk
28.1 parts kaolin.

c)
25 parts active substance
2.5 parts isooctylphenoxy-polyoxyethylene-ethanol
1.7 parts champagne chalk-hydroxyethyl cellulose mix (1:1)
8.3 parts sodium aluminium silicate
16.5 parts kieselguhr
46 parts kaolin.

d)
10 parts active substance
3 parts mixture of sodium salts of fatty alcohol sulphates
5 parts naphthalene sulphonic acid formaldehyde condensate 82 parts kaolin.

The active substances were intimately mixed in suitable mixers with the additive materials and milled on suitable mills and rolls. Wettable powders were obtained which could be diluted with water to suspensions of any desired concentration.

Emulsifiable concentrate: for manufacturing an a) 10 percent and b) 25 percent emulsifiable concentrate, the following materials were used:

a)
10 parts active substance,
3.4 parts epoxidised vegetable oil,
13.4 parts of a combination emulsifier consisting of fatty alcohol polyglycol ethers and calcium alkyl aryl sulphonates
40 parts dimethylformamide
43.2 parts xylene.

b)
25 parts active substance acid ester
2.5 parts epoxidised vegetable oil
10 parts of an alkyl aryl sulphonate-fatty alcohol polyglycol ether mixture
5 parts dimethylformamide
57.5 parts xylene.

Emulsions of any desired concentration could be made from these concentrations by dilution with water.
Spraying agent: for making a 5 percent spraying agent the following components were used:
5 parts active substance
1 part epichlorohydrin
94 parts petrol (boiling range 160°–190°C).

The materials described can also be mixed with other biocidally active substances or agents. Thus, the new agents can contain, apart from the noted compounds of general formula I, for example, insecticides for broadening the spectrum of activity.

The following examples will serve to illustrate the invention:

EXAMPLE 1

1a. 21.7g 1-bromo-3,7-dimethyl-2,6-octadiene was added to a solution of 15.2g 3-propargyloxyphenol (boiling point 84°–85°C/0.02 torr $n_D^{20}$ : 1,5640) in 150 ml pure 1,2-dimethoxyethane, and immediately thereafter with stirring at 20°–22°C a solution of 6.4g 85% potassium hydroxide in 100 ml absolute ethanol was added dropwise. The addition of potassium hydroxide solution (lasting about 8 hours) was so regulated that the reaction mixture always remained weakly alkaline (pH about 8–9). After the addition of the base the mixture was stirred further for 16 hours at room temperature and then warmed for one hour to 70°C and thereafter cooled and filtered from the precipitated potassium bromide. The filtrate was reduced to about 50 ml, taken up in a diethyl ether hexane mixture (1:4) washed 3 times with 30 ml 10% aqueous potassium hydroxide and then washed neutral with water. The organic phase was dried over sodium sulphate and the solvent distilled off in vacuum. The remaining 1(3-propargyloxy)phenoxy-3,7,dimethyl-2,6-octadiene was purified by chromatography on silica gel (activity III) with an ether hexane mixture (1:5) $n_D^{20}$ 1.5326. This ether can also be purified by high vacuum distillation.

The 3-propargyloxyphenol used for the manufacture of 1-(3-propargyloxy)phenoxy-3,7-dimethyl-2,6-octadiene can be manufactured in the following fashion: 165 g of propargylchloride were added dropwise with stirring and within 2 hours to a mixture of 220 g resorcinol 305 g anhydrous potassium carbonate, 7.3 g finely divided potassium iodide and 700 ml acetone, under a nitrogen atmosphere at the boiling temperature of acetone. Thereafter the mixture was boiled under reflux for a further 14 hours. The reaction mixture was then diluted with 800 ml acetone, filtered clear and the filtrate reduced. The residue was taken up in 1500 ml toluene and the toluene solution was repeatedly washed with 200 ml each time of warm water at 40°–50°C. After drying the toluene solution over sodium sulphate and the addition of some active carbon the mixture was filtered, the filtrate freed from the solvent in vacuo and the residue dissolved in 1000 ml ether. The ether solution was washed three times with 200 ml 30% ice-cold caustic soda and thereafter twice with water. The purified aqueous alkali phases were then washed again twice with a little ether. The aqueous alkaline phase which contained the sodium salt of 3-propargyloxyphenol was now allowed to flow with vigorous stirring to a mixture of 100 ml chloroform, 1 kilogram ice and 600 ml concentrated hydrochloric acid. The phases were separated, the aqueous hydrochloric acid phase subsequently washed once with chloroform, the purified chloroform phase washed briefly with water, dried over sodium sulphate and the solvent distilled off. The residue was then fractionally distilled in vacuum by means of which the colourless 3-propargyloxyphenol of boiling point 84°–85°C/0,02 torr was obtained.

EXAMPLE 2

To a solution of 14.6 g 4-(3,7-dimethyl-2,6-nonadienyl-1-oxy) benzophenone ($n_D^{20}$ : 1.5763) in 160 ml dichloromethane there was added at −2° to 0°C within six hours a solution of 8.6 g 85% 3-chloroperbenzoic acid in 90 ml dichloromethane dropwise. After a further three hours stirring at 0° to 5°C the reaction mixture was diluted with ether, the solution repeatedly washed with ice-cold 10% aqueous caustic potash and then washed neutral with water. After drying the organic phase over sodium sulphate the solvent was distilled off in vacuum and the remaining 4-(6,7-epoxy-3,7-dimethyl-2-nonenyl-1-oxy) benzophenone chromatographically purified on silica gel with ether hexane (2.3). $n_D^{20}$ : 1.5717.

The 4-(3,7-dimethyl-2,6-nonadienyl-1-oxy)benzophenone used as a starting product can be manufactured in the following way: a solution of 6.3 g about 90% potassium hydroxide in a 100 ml absolute ethanol were added dropwise over a period of 7 hours to a solution of 23.2 g 1-bromo-3,7-dimethyl-2,6-nonadiene and 19.8 g 4-hydroxybenzophenone in 160 ml 1,2-dimethoxyethane, so that the reaction mixture always showed an alkaline reaction and stirring was then continued for 14 hours at room temperature. For finishing, the precipitated potassium bromide was filtered off, the filtrate reduced, the residue taken up in 200 ml ether, washed four times with ice-cold 10% caustic potash and then washed neutral with water. After drying the ether solution over sodium sulphate the solvent was removed in vacuum and the residue purified by chromatography on silica gel (ether hexane 1:3) whereby the 4-(3,7-dimethyl-2,6-nonadienyl-1-oxy)-benzophenone was obtained. $n_D^{20}$ = 1,5673.

EXAMPLE 3

A solution of 5.2 g thionyl chloride in 15 ml absolute ether was added dropwise at 0°C with stirring within 1 hour to a mixture of 11g 1-(4-carboxy)phenoxy-3,7-dimethyl-2,6-octadiene and 3.5 g. absolute pyridine in 100 ml absolute ether. After that the reaction mixture was stirred for a further hour at room temperature and the precipitated pyridine hydrochloride was then filtered out with exclusion of moisture and with the aid of a filtering agent such as Hyflo. The filtrate was reduced in vacuo at at most 30°C, the residue taken up in 40 ml absolute benzene and added dropwise at 0°–5°C to a solution of about 20 g dry methyl mercaptan and 3.5 g absolute pyridine in 25 mol absolute benzene and 60 ml hexane. The mixture was stirred further overnight at room temperature, and then reduced in vacuum, taken up in ether hexane (1:3) and then washed with ice-cold 0.1 N - hydrochloric acid, 10% ice-cold potassium carbonate solution and water, dried over sodium sulphate and evaporated. Chromatography of the residue on silica gel (elution agent: ether hexane 1:5) gave the 1-(4-methyl-5-carbonyl)phenoxy 3,7-dimethyl-2,6-octadiene. Melting point 35°–37°C (from hexane).

The 1-(4-carboxy)-phenoxy-3,7-dimethyl-2,6-octadiene serving as a starting material can be manufactured as follows: a solution of 27.6 g 4-hydroxybenzoic acid in 330 ml 1,2dimethoxyethane was treated with stirring at room temperature within 15 minutes with a solution of 12.6 g about 90% potassium hydroxide in a 175 ml absolute ethanol. Immediately thereafter there was added with stirring at room temperature and dropwise from two dropping funnels within six hours regularly 43.5 g 1-bromo-3,7-dimethyl-2,6-octadiene and a further 12.6g of about 90% potassium hydroxide in 175 ml absolute ethanol. After the dropwise addition the mixture was stirred overnight at room temperature and for a further 3 hours at 40°C. For finishing, the reaction mixture was treated with 200 ml

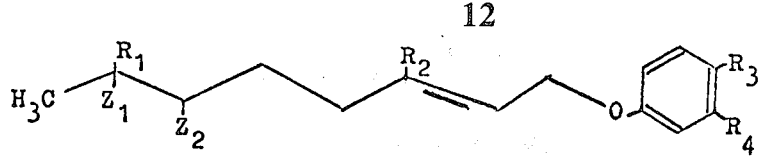

(C—C— means a carbon carbon bond; —O— means an oxygen bridge).

| R$_4$ | R$_3$ | R$_2$ | R$_1$ | Z$_1$; Z$_2$ | Physical data |
|---|---|---|---|---|---|
| H | -CO-⟨phenyl⟩ | CH$_3$ | CH$_3$ | —C—C— | $n_D^{20} = 1,5799$ |
| H | -CO-⟨phenyl⟩ | CH$_3$ | CH$_3$ | —O— | $n_D^{20} = 1,5756$ |
| H | —OCH$_2$—CH=CH$_2$ | CH$_3$ | CH$_3$ | —C—C— | $n_D^{20} = 1,5252$ |
| H | —OCH$_2$—CH=CH$_2$ | CH$_3$ | CH$_3$ | —O— | $n_D^{20} = 1,5195$ |
| H | —O—CH$_2$—C(Cl)=CH$_2$ | CH$_3$ | CH$_3$ | —C—C— | $n_D^{20} = 1,5320$ |
| H | —O—CH$_2$—C(Cl)=CH$_2$ | CH$_3$ | CH$_3$ | —O— | $n_D^{20} = 1,5264$ |
| H | -O-⟨phenyl⟩ | CH$_3$ | CH$_3$ | —C—C— | $n_D^{20} = 1,5551$ |
| H | -O-⟨phenyl⟩ | CH$_3$ | CH$_3$ | —O— | $n_D^{20} = 1,5506$ |
| H | -O-CH$_2$-⟨phenyl⟩ | CH$_3$ | CH$_3$ | —C—C— | M.pt. = 67–70°C |
| H | -O-CH$_2$-⟨phenyl⟩ | CH$_3$ | CH$_3$ | —O— | $n_D^{20} = 1,5520$ |
| H | —CH$_2$—C$_6$H$_5$ | CH$_3$ | CH$_3$ | —C—C— | $n_D^{20} = 1,5539$ |
| H | —CH$_2$—C$_6$H$_5$ | CH$_3$ | CH$_3$ | —O— | $n_D^{20} = 1,5494$ |
| —OCH$_2$—C≡CH | H | CH$_3$ | CH$_3$ | —O— | $n_D^{20} = 1,5273$ |
| H | \OCH$_2$/CH=CH—Cl (cyclic) | CH$_3$ | CH$_3$ | —C—C— | $n_D^{20} = 1,5380$ |
| H | \OCH$_2$/CH=CH—Cl (cyclic) | CH$_3$ | CH$_3$ | —O— | $n_D^{20} = 1,5298$ | water, the 1,2-dimethoxyethane substantially sucked off in vacuo and the aqueous solution adjusted with N-hydrochloric acid to a pH of about 2, whereon the 1-(4-carboxy)-phenoxy-3,7-dimethyl-2,6-octadiene precipitated out. The precipitate was separated, dried, then well washed with hexane, filtered off again and dried. For further purification the dry crude product was dissolved in a mixture of ether and methyl acetate (1:4) and the clear filtered solution evaporated in vacuo and the residue recrystallised from cyclohexane. Melting point 113°–116°C.

The 1-(4-carboxy)phenoxy-3,7-dimethyl-2,6-octadiene can likewise be obtained by alkaline hydrolysis of a 1-(4-alkoxycarbonyl)phenoxy-3,7-dimethyl-2,6-octadiene compound.

In a fashion similar to examples 1 – 3, the following compounds were also manufactured:

EXAMPLE 4

10 larvae of Dysdercus fasciatus, which were 8–10 days before the adult moult, were topically treated with acetonic active substance solutions. The test animals were then kept at 28°C and 80–90 percent relative humidity. As food, the Dysdercus fasciatus larvae had groats from preswollen cotton seeds.

After about 10 days, i.e. as soon as the control animals had completed their adult moult, the test animals were evaluated. Apart from normal adults and dead larvae special forms were to be found such as extra larvae (larvae with an additional larvae skin) and adultoids (adults with larval features). In the special types it is a question of non-viable stages of developments which are not to be found in the normal cycle of development.

From the following table the number of normal adults is evident which were to be found at the various concentrations given:

| Compound | Amount of Active Substance in γ | Dysdercus fasciatus |
|---|---|---|
| 1-(4-Acetylamino)-phenoxy-6,7-epoxy-3,7-dimethyl-2-octene | 5 | 0 |
| | 0,5 | 3 |
| 4-(3,7-Dimethyl-2,6-octadienyl-1-oxy)-benzophenone | 5 | 0 |
| | 0,5 | 2 |
| 4-(3,7-Dimethyl-6,7-epoxy-2-octenyl-1-oxy)-benzophenone | 5 | 0 |
| | 0,5 | 0 |
| 4-(3,7-Dimethyl-2,6-nonadienyl-1-oxy)-benzophenone | 5 | 0 |
| 4-(3,7-Dimethyl-6,7-epoxy-2-nonenyl-1-oxy)-benzophenone | 5 | 0 |
| | 0,5 | 0 |
| 1-(4-benzyl)-phenoxy-6,7-epoxy-3,7-dimethyl-2-octene | 5 | 0 |
| 1-[4-(2-Propen-1-oxy)]-phenoxy-6,7-epoxy-3,7-dimethyl-2-octene | 5 | 0 |
| 1-[4-(2-Chlor-2-propen-1-oxy)]phenoxy-6,7-epoxy-3,7-dimethyl-2-octene | 5 | 0 |
| 1-[4-(3-Chlor-2-propen-1-oxy)]-phenoxy-6,7-epoxy-3,7-dimethyl-2-octene | 5 | 0 |
| 1-(3-Propargyloxy)-phenoxy-3,7-dimethyl-2,6-octadiene | 5 | 0 |
| 1-(3-Propargyloxy)-phenoxy-6,7-epoxy-3,7-dimethyl-2-octene | 5 | 0 |
| | 0,5 | 0 |
| 1-(4-Methallyloxy)-phenoxy-3,7-dimethyl-6,7-epoxy-2-octene | 5 | 0 |
| 1-[4-(Methylthio)carbonyl]-phenoxy-3,7-dimethyl-2,6-octadiene | 5 | 0 |
| Control | — | 10 |

EXAMPLE 5

In each test 10 fresh pupae of Dermestes lardarius were topically treated with solutions of active substance in acetone. The pupae were then kept at 28° C and 80–90 percent relative humidity.

After about 10 days, i.e. as soon as the control animals had left the pupal casing as Imagines, the test animals were evaluated; as well as normal adults and dead pupae adultoids (adults with larval characteristics) were found.

The adultoids were not viable stages of development and they are not to be found in the normal cycle of development. In the following table the number of normal adults is given which were to be found at the various concentrations given.

| Compound | Amount of Active Substance in γ | Dermestes Lardarius |
|---|---|---|
| 1-(4-Benzyl)-phenoxy-6,7-epoxy-3,7-dimethyl-2-octene | 5 | 0 |
| 1-[4-(2-Propen-1-oxy)]-phenoxy-6,7-epoxy-3,7-dimethyl-2-octene | 5 | 0 |
| | 0,5 | 0 |
| 1-(3-Propargyloxy)-phenoxy-3,7-dimethyl-2,6-octadiene | 5 | 3 |
| Control | — | 10 |

EXAMPLE 6

In each case 10 fresh pupae of Tenebrio molitor were topically treated with active substance solutions in acetone. The pupae were then kept at 28°C and 80–90 percent relative humidity. After about 10 days, i.e. as soon as the control animals had left the pupal skin as Imagines, the test animals were evaluated. As well as normal adults and dead pupae, adultoids were found (adults with larval features).

The adultoids were not viable stages of developments and they are not to be found in the normal cycle of development. In the following table the number of normal adults is given which were to be found at the various concentrations given.

| Compound | Amount of Active Substance in γ | Tenebrio molitor |
|---|---|---|
| 4-(3,7-Dimethyl-6,7-epoxy-2-octenyl-1-oxy)-benzophenone | 5 | 1 |
| | 0,5 | 2 |
| 1-[4-(2-Propen-1-oxy)]-phenoxy-6,7-epoxy-3,7-dimethyl-2-octene | 5 | 1 |
| | 0,5 | 0 |
| Control | — | 10 |

EXAMPLE 7

10 fresh pupae each of Leptinotarsa decemlineata were topically treated with solutions of active substance in acetone The pupae were then kept at 28° C and 80–90 percent relative humidity After about 10 days i.e. as soon as the control animals had left the pupal casing as imagines, the test animals were evaluated. As well as normal adults and dead pupae, adultoids were found (adults with larval features). In the case of adultoids they are not viable stages of development and are not to be found in the normal cycle of developments. In the following table the number of normal adults is given which were to be found at the various concentrations given.

| Compound | Amount of Active Substance in γ | Leptinotarsa decemlineata |
|---|---|---|
| 1-[4-(2-Propen-1-oxy)]-phenoxy-6,7-epoxy-3,7-dimethyl-2-octene | 5 | 0 |
| | 0,5 | 0 |
| Control | — | 10 |

What we claim is:
1. A compound of the formula

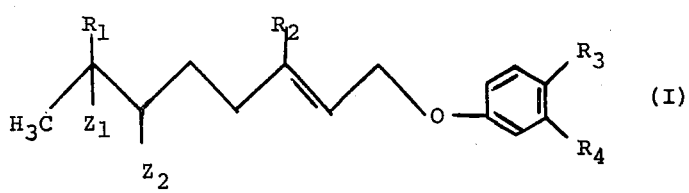
wherein
Z₁ and Z₂ together are an oxygen bridge,
R₁ and R₂ are each methyl or ethyl,
R₃ is hydrogen and R₄ represents propargyloxy.
2. The compound according to claim 1 which has the formula
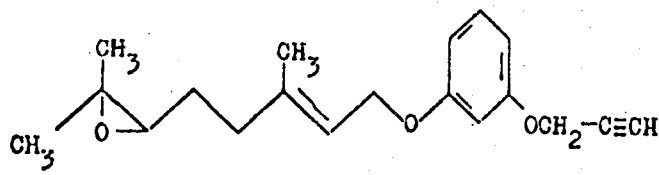
* * * * *